US011131676B2

(12) United States Patent
Alaedini

(10) Patent No.: US 11,131,676 B2
(45) Date of Patent: Sep. 28, 2021

(54) SYSTEMIC IMMUNE ACTIVATION AND BIOMARKERS OF NONCELIAC WHEAT/GLUTEN SENSITIVITY

(71) Applicant: THE TRUSTEES OF COLUMBIA UNIVERSITY IN THE CITY OF NEW YORK, New York, NY (US)

(72) Inventor: Armin Alaedini, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 201 days.

(21) Appl. No.: 16/079,321

(22) PCT Filed: Feb. 24, 2017

(86) PCT No.: PCT/US2017/019292
§ 371 (c)(1),
(2) Date: Aug. 23, 2018

(87) PCT Pub. No.: WO2017/147378
PCT Pub. Date: Aug. 31, 2017

(65) Prior Publication Data
US 2019/0056411 A1 Feb. 21, 2019

Related U.S. Application Data

(60) Provisional application No. 62/299,609, filed on Feb. 25, 2016.

(51) Int. Cl.
*G01N 33/50* (2006.01)
*G01N 33/68* (2006.01)
*C07K 16/16* (2006.01)
*G01N 33/53* (2006.01)
*G01N 33/92* (2006.01)
*G01N 33/564* (2006.01)

(52) U.S. Cl.
CPC ......... *G01N 33/6893* (2013.01); *C07K 16/16* (2013.01); *G01N 33/53* (2013.01); *G01N 33/564* (2013.01); *G01N 33/92* (2013.01); *G01N 2333/4703* (2013.01); *G01N 2333/70596* (2013.01); *G01N 2800/02* (2013.01); *G01N 2800/24* (2013.01); *G01N 2800/52* (2013.01)

(58) Field of Classification Search
None
See application file for complete search history.

(56) References Cited

U.S. PATENT DOCUMENTS 8,409,819 B1  4/2013  Barken
2012/0190571 A1*  7/2012  Vojdani .............. G01N 33/6854
506/9

2014/0037661 A1  2/2014  Baar et al.
2014/0186855 A1  7/2014  Vojdani
2016/0377629 A1  12/2016  Vojdani

OTHER PUBLICATIONS

Volta et al., Non-celiac gluten sensitivity: questions still to be answered despite increasing awareness, Cellular & Molecular Immunology vol. 10, pp. 383-392(2013) (Year: 2013).*
And Severance et al., Discordant patterns of bacterial translocation markers and implications for innate immune imbalances in schizophrenia, Schizophrenia Research 148 (2013) 130-137 (Year: 2013).*
Lionetti et al., Gluten Psychosis: Confirmation of a New Clinical Entity, Nutrients 2015, 7, 5532-5539. (Year: 2015).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, , pp. 1-7. (Year: 2014).*
Carroccio et al. "Non-celiac wheat sensitivity as an allergic condition: personal experience and narrative review," American Journal of Gastroenterology, Nov. 5, 2013 (Nov. 5, 2013), vol. 108, No. 12, pp. 1845-1852. entire document.
Catassi et al. "Non-Celiac Gluten Sensitivity: The New Frontier of Gluten Related Disorders," Nutrients, Sep. 26, 2013 (Sep. 26, 2013), vol. 5, pp. 3839-3853. entire document.
Catassi C, Elli L, Bonaz B, et al. Diagnosis of non-celiac gluten sensitivity (NCGS): the Salerno experts' criteria. Nutrients Jun. 2015;7:4966-77.
Caio G, Volta U, Tovoli F, et al. Effect of gluten free diet on immune response to gliadin in patients with non-celiac gluten sensitivity. BMC Gastroenterol Feb. 13, 2014;14:26.
Volta U, Caio G, De Giorgio R, et al. Non-celiac gluten sensitivity: a work-in-progress entity in the spectrum of wheat-related disorders. Best Pract Res Clin. Gastroenterol Jun. 2015;29:477-91.
Volta U, Bardella MT, Calabro A, et al. An Italian prospective multicenter survey on patients suspected of having non-celiac gluten sensitivity. BMC Med May 23, 2014;12:85.
Rubio-Tapia A, Hill ID, Kelly CP, et al. ACG clinical guidelines: diagnosis and management of celiac disease. Am J Gastroenterol May 2013;108:656-76.

(Continued)

*Primary Examiner* — Gary Counts
(74) *Attorney, Agent, or Firm* — Leason Ellis LLP

(57) ABSTRACT

The present invention provides a method of using increased levels of one or more biomarkers to identify subjects having non-celiac gluten sensitivity or non-celiac wheat sensitivity. The identification would aid the physician or health professional to determine a specific treatment for the patient, for example, a diet that eliminates wheat, rye, and/or barley. In one embodiment, the biomarkers are one or more of soluble CD 14 (sCD14), lipopolysaccharide-binding protein (LBP), anti-lipopolysaccharide antibodies, anti-flagellin antibodies, anti-gliadin antibodies, and intestinal fatty acid-binding protein (FABP2). The present invention also provides a method of using the same markers to monitor the response to treatment for non-celiac wheat sensitivity in a subject.

4 Claims, 11 Drawing Sheets

(56) References Cited

OTHER PUBLICATIONS

Moeller S, Canetta PA, Taylor AK, et al. Lack of serologic evidence to link IgA nephropathy with celiac disease or immune reactivity to gluten. PLoS One Apr. 14, 2014;9:e94677.

Lau N, Green PH, Taylor AK, et al. Markers of celiac disease and gluten sensitivity in children with autism. PLoS One Jun. 18, 2013;8:e66155.

Huebener S, Tanaka CK, Uhde M, et al. Specific nongluten proteins of wheat are novel target antigens in celiac disease humoral response. J Proteome Res Jan. 2, 2015; 14:503-11.

Brenchley JM, Douek DC. Microbial translocation across the GI tract. Annu Rev Immunol Dec. 3, 2012;30: 149-73.

Miller SI, Ernst RK, Bader MW. LPS, TLR4 and infectious disease diversity. Nat Rev Microbiol Jan. 2005;3:36-46.

Barclay GR. Endogenous endotoxin-core antibody (EndoCAb) as a marker of endotoxin exposure and a prognostic indicator: a review. Prog Clin Biol Res 1995;392:263-72.

Akira S, Takeda K. Toll-like receptor signalling. Nat Rev Immunol Jul. 2004;4:499-511.

Chen Z, Jalabi W, Shpargel KB, et al. Lipopolysaccharide-induced microglial activation and neuroprotection against experimental brain injury is independent of hematogenous TLR4. J Neurosci Aug. 22, 2012;32: 11706-15.

Sandler NG, Douek DC. Microbial translocation in HIV infection: causes, consequences and treatment opportunities. Nat Rev Microbiol Sep. 2012;10:655-66.

Pelsers MM, Hermens WT, Glatz JF. Fatty acid-binding proteins as plasma markers of tissue injury. Clin Chim Acta Feb. 2005;352:15-35.

Pelsers MM, Namiot Z, Kisielewski W, et al. Intestinal-type and liver-type fatty acid-binding protein in the intestine. Tissue distribution and clinical utility. Clin Biochem Oct. 2003;36:529-35.

Sandler NG, Koh C, Roque A, et al. Host response to translocated microbial products predicts outcomes of patients with HBV or HCV infection. Gastroenterology Oct. 2011; 141: 1220-30.

Sacchettini JC, Hauft SM, Van Camp SL, et al. Developmental and structural studies of an intracellular lipid binding protein expressed in the ileal epithelium. J Biol Chem Nov. 5, 1990;265: 19199-207.

Adriaanse MP, Tack GJ, Passes VL, et al. Serum I-FABP as marker for enterocyte damage in coeliac disease and its relation to villous atrophy and circulating autoantibodies. Aliment Pharmacol Therapeutics Jan. 7, 2013;37:482-90.

Hunt PW, Sinclair E, Rodriguez B, et al. Gut epithelial barrier dysfunction and innate immune activation predict mortality in treated HIV infection. J Infect Dis Oct. 15, 2014;210:1228-38.

Estes JD, Harris LD, Klatt NR, et al. Damaged intestinal epithelial integrity linked to microbial translocation in pathogenic simian immunodeficiency virus infections. PLoS Pathog Aug. 19, 2010;6:e1001052.

Shahbazkhani B, Sadeghi A, Malekzadeh R, et al. Non-Celiac Gluten Sensitivity Has Narrowed the Spectrum of Irritable Bowel Syndrome: A Double-Blind Randomized Placebo-Controlled Trial. Nutrients Jun. 5, 2015;7:4542-54.

Carroccio A, Mansueto P, Iacono G, et al. Non-celiac wheat sensitivity diagnosed by doubleblind placebo-controlled challenge: exploring a new clinical entity. Am J Gastroenterol Dec. 2012;107: 1898-906.

Cossart P, Sansonetti PJ. Bacterial invasion: the paradigms of enteroinvasive pathogens. Science Apr. 9, 2004;304:242-8.

Kiesslich R, Goetz M, Angus EM, et al. Identification of epithelial gaps in human small and large intestine by confocal endomicroscopy. Gastroenterology Dec. 2007;133:1769-78.

Lanzavecchia A, Bernasconi N, Traggiai E, et al. Understanding and making use of human memory B cells, Immunol Rev Jun. 2006;211:303-9.

Capolunghi F, Rosado MM, Sinibaldi M, et al. Why do we need IgM memory B cells? Immunol Lett May 2013;152:114-20.

Bailey M, Haverson K, Miller B, et al. Effects of infection with transmissible gastroenteritis virus on concomitant immune responses to dietary and injected antigens. Clin Diagn Lab Immunol Mar. 2004;11:337-43.

Ehrenstein MR, Notley CA. The importance of natural IgM: scavenger, protector and regulator. Nat Rev Immunol Nov. 2010; 10:778-86.

Katz KD, Rashtak S, Lahr BD, et al. Screening for celiac disease in a North American population: sequential serology and gastrointestinal symptoms. Am J Gastroenterol Jul. 2011; 106:1333-9.

Leffler DA, Dennis M, Hyett B, et al. Etiologies and predictors of diagnosis in nonresponsive celiac disease. Clin Gastroenterol Hepatol Apr. 2007;5:445-50.

\* cited by examiner

Figures 1A-F
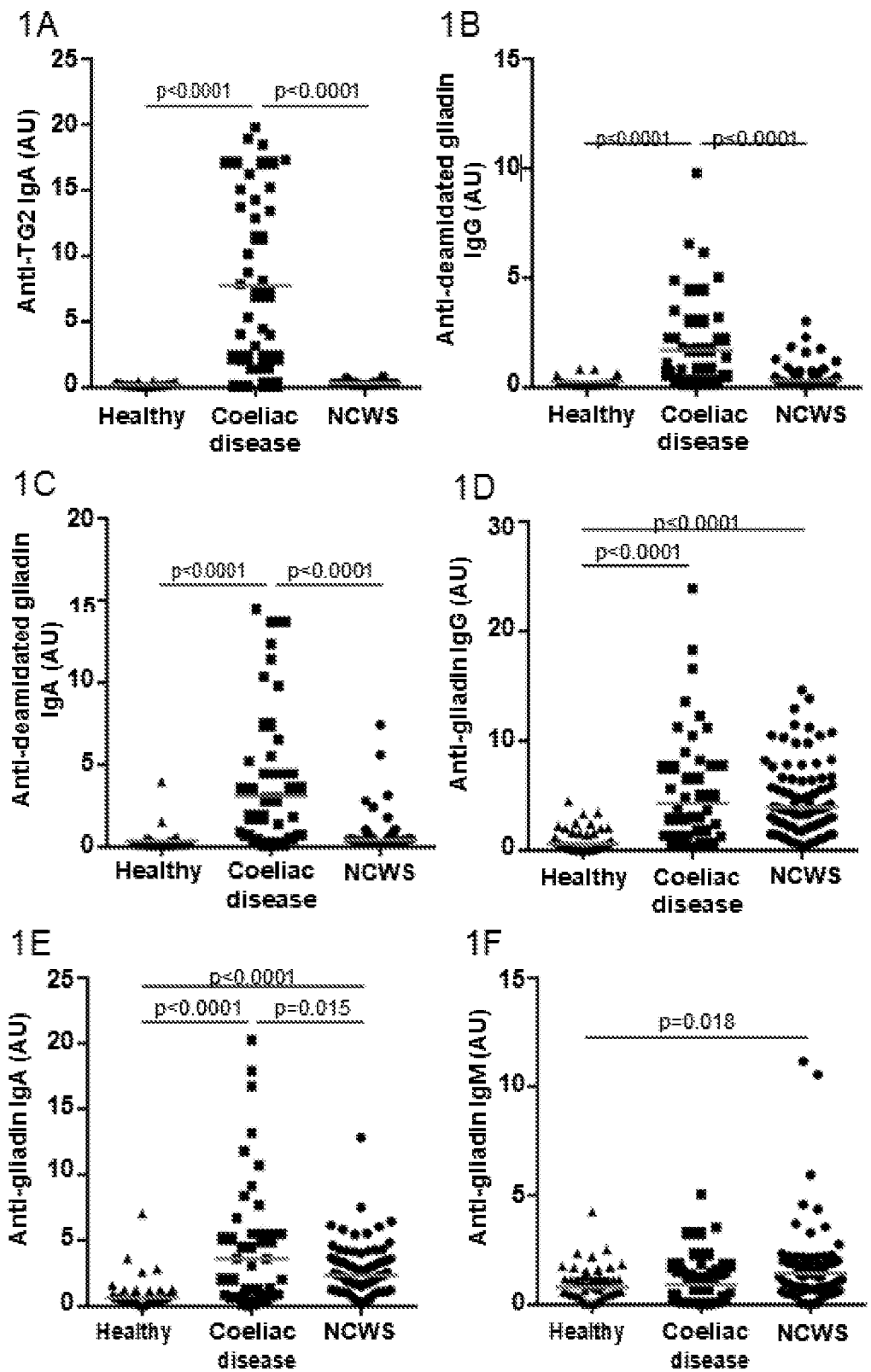

Figures 2A-F
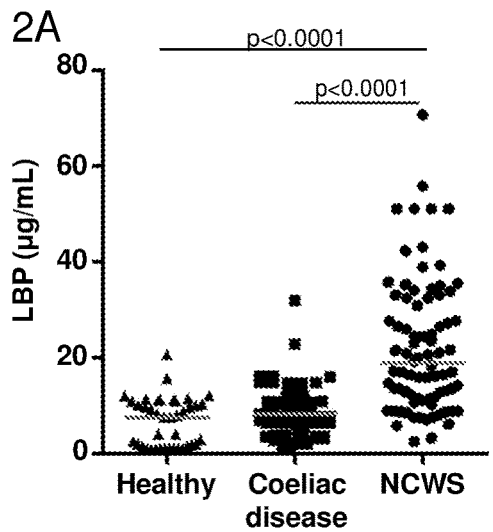
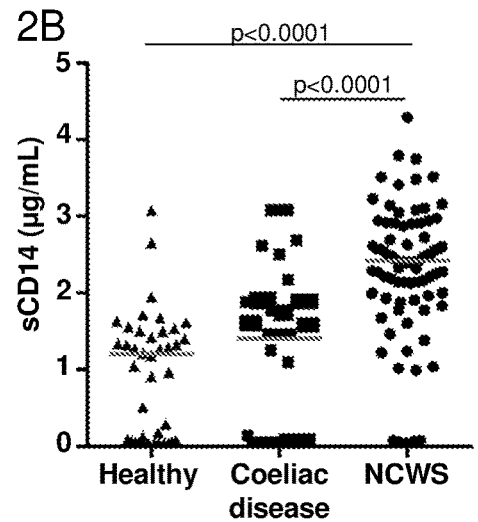
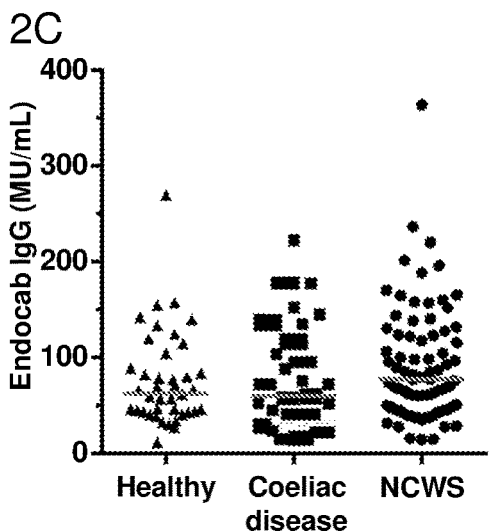
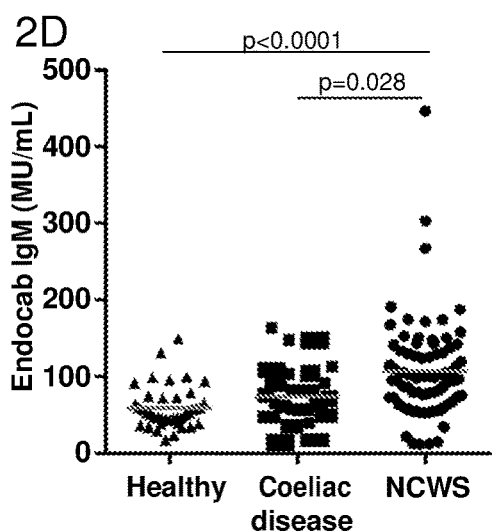
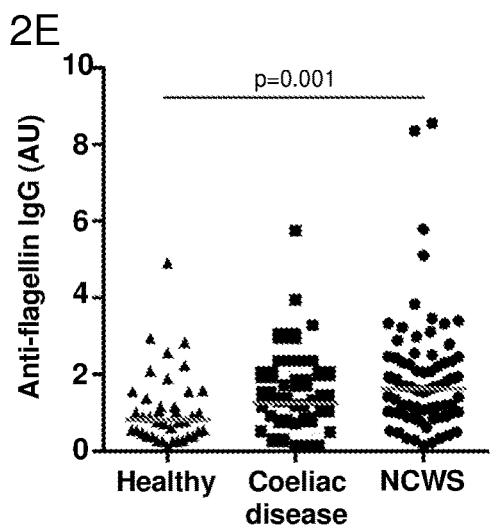
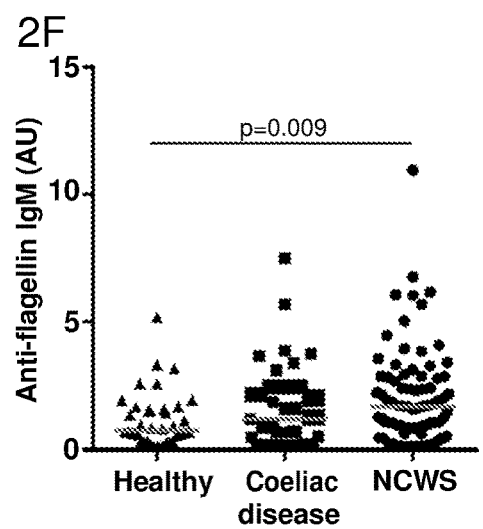

Figures 3A-C
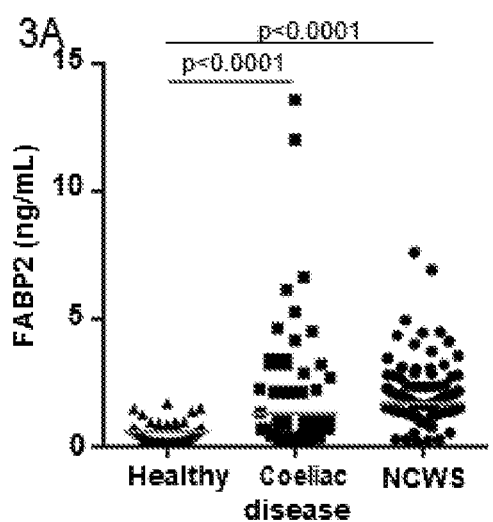
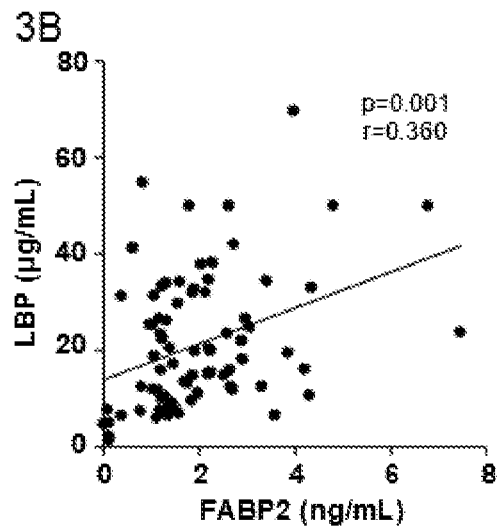
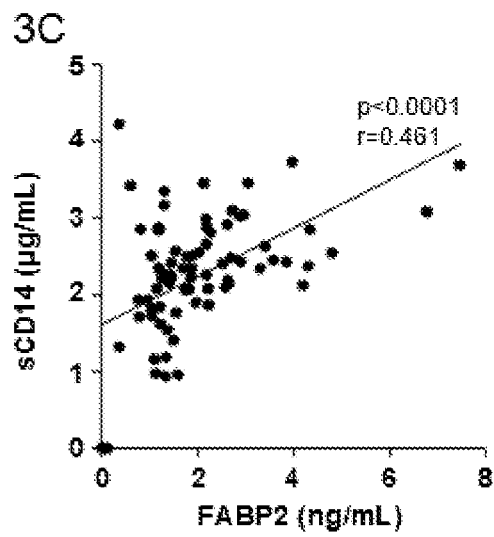

Figures 10A-B
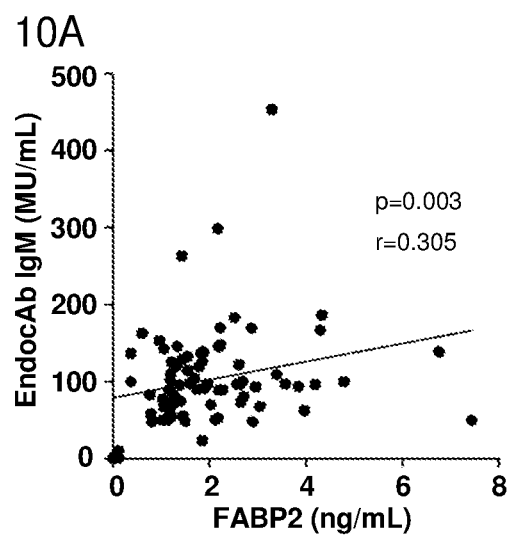
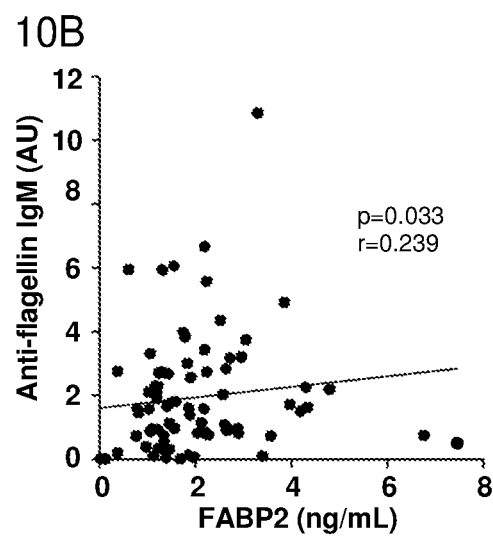

SYSTEMIC IMMUNE ACTIVATION AND BIOMARKERS OF NONCELIAC WHEAT/GLUTEN SENSITIVITY

CROSS-REFERENCE TO RELATED PATENT APPLICATIONS

This application is a U.S. National Phase Application under 35 U.S.C. § 371 of International Patent Application No. PCT/US2017/019292, filed Feb. 24, 2017, which claims the benefit of U.S. Ser. No. 62/299,609, filed Feb. 25, 2016, each of which are incorporated by reference as if expressly set forth in their respective entirety herein. The International Application was published in English on Aug. 31, 2017 as WO 2017/147378.

Throughout this application, various references or publications are cited. Disclosures of these references or publications in their entireties are hereby incorporated by reference into this application in order to more fully describe the state of the art to which this invention pertains.

GOVERNMENT SUPPORT CLAUSE

This invention was made with government support under grant TR000040. The government has certain rights in the invention.

FIELD OF THE INVENTION

This invention relates in general to the mechanisms behind the onset of non-celiac gluten sensitivity (NCGS) or non-celiac wheat sensitivity (NCWS) and relevant biomarkers therefor.

BACKGROUND OF THE INVENTION

Celiac disease is a common autoimmune disorder with genetic, environmental, and immunologic components. It is characterized by an immune response to ingested wheat gluten and related proteins of rye and barley that leads to inflammation, villous atrophy, and crypt hyperplasia in the small intestine. Among the most common manifestations of celiac disease are abdominal pain, diarrhea, weight loss, bone disease, and anemia. The disease is strongly associated with genes for the specific class II human leukocyte antigens (HLA) DQ2 and DQ8 that are involved in presenting specific immunogenic peptides of gluten proteins to $CD4^+$ T cells in the small intestine. Transglutaminase 2 (TG2) appears to be an important player in the disease, both as a deamidating enzyme that can enhance the immunostimulatory effect of gluten, and as a target autoantigen in the ensuing immune response. The major B cell responses in patients with celiac disease target native and deamidated gluten sequences, as well as the TG2 autoantigen. Among these, the IgA anti-TG2 antibody is currently considered the most sensitive and specific serologic marker, whereas antibodies to native gluten proteins have low specificity for celiac disease and have been reported to be elevated in a number of other conditions.

Some individuals experience a range of symptoms in response to ingestion of wheat and related cereals, yet lack the characteristic serologic, histologic, or genetic markers of celiac disease. The terms non-celiac gluten sensitivity (NCGS) or non-celiac wheat sensitivity (NCWS) are generally used to refer to this condition, which is currently understood as the collection of non-specific symptoms in response to ingestion of gluten-containing cereals, and the resolution of such symptoms upon removal of those foods from diet in individuals in whom celiac disease and IgE-mediated wheat allergy have been ruled out. The condition is associated with gastrointestinal symptoms, most commonly including bloating, abdominal pain, and diarrhea, as well as certain extra-intestinal symptoms, among which fatigue, headache, anxiety, and cognitive difficulties feature prominently. Accurate figures for the prevalence of NCWS are not available, although estimates that put the number at similar to or greater than for celiac disease (1%) are often cited. Despite the commonly used terminology for the condition, the identity of the component(s) of wheat and/or related cereals responsible for triggering the associated symptoms remains uncertain. While recent controlled trials have indicated a prominent role for gluten, non-gluten proteins and fermentable short chain carbohydrates have also been suggested by some studies to drive aberrant immune responses or to be associated with symptoms.

The potential mechanisms behind the onset of symptoms in NCWS remain unknown and no biomarkers have been identified. However, a small number of studies point to increased antibody reactivity to gluten proteins, moderately raised intraepithelial lymphocyte numbers, increased intraepithelial and lamina propria eosinophil infiltration, and enhanced expression of intestinal tight junction protein claudin 4, Toll-like receptor 2 (TLR2), or IFN-γ, suggesting intercellular junction and/or immune abnormalities in subsets of affected individuals. Human intestinal epithelial surfaces are colonized by large communities of microorganisms and are in constant contact with an abundance of highly immunogenic microbial products. Compromised intestinal epithelial integrity has been linked to extensive systemic innate and adaptive immune responses that are a consequence of microbial translocation from the lumen into circulation. Systemic immune activation in response to microbial translocation is a noted component of HIV infection and inflammatory bowel disease.

Therefore, there is a need to determine the mechanisms behind the onset of symptoms in NCWS and relevant biomarkers for accurate diagnosis of NCWS.

SUMMARY OF THE INVENTION

The present invention arises from studies that examined whether sensitivity to wheat in the absence of celiac disease is associated with systemic immune activation in response to translocated microbial products that may be linked to an enteropathy. The studies led to identification of a panel of biomarkers that would be useful for accurate diagnosis of NCWS.

Study participants included individuals who reported intestinal and/or extra-intestinal symptoms in response to the ingestion of wheat and in whom celiac disease and wheat allergy were ruled out (n=80), patients with biopsy-confirmed celiac disease (n=40), and healthy controls (n=40). A subset of individuals with sensitivity to wheat underwent six months of a self-monitored diet that excluded wheat, rye, and barley (n=20). Blood serum samples were analyzed for markers of intestinal cell damage and systemic immune response to microbial products.

In comparison to healthy controls and celiac disease patients, individuals with wheat sensitivity had significantly increased serum levels of soluble CD14 (sCD14) and lipopolysaccharide (LPS)-binding protein (LBP), as well as antibody reactivity to bacterial LPS and flagellin and to wheat gluten. Circulating levels of intestinal fatty acid-binding protein (FABP2), a marker of intestinal epithelial cell damage, were significantly elevated in the affected individuals and correlated with the innate and adaptive immune responses to bacterial products. There was a significant change towards normalization of the levels of FABP2 and immune activation markers following the restrictive diet. These data reveal a state of enhanced systemic immune response to microbial products in conjunction with a compromised intestinal epithelium affecting a subset of individuals who experience sensitivity to wheat in the absence of celiac disease.

The results demonstrate the presence of objective markers of systemic immune activation and epithelial cell damage in individuals who report sensitivity to wheat in the absence of celiac disease. The principal component analysis (PCA) of the entire dataset demonstrated that the identified panel of biomarkers was capable of clustering the healthy control, celiac disease, and NCWS subjects into three distinctly discernible groups.

BRIEF DESCRIPTION OF THE DRAWINGS

FIGS. 1A-F show markers of celiac disease and immune reactivity to wheat gluten. Serum levels of IgA antibody to TG2 (FIG. 1A), IgG antibody to deamidated gliadin (FIG. 1B), IgA antibody to deamidated gliadin (FIG. 1C), IgG antibody to native gliadin (FIG. 1D), IgA antibody to native gliadin (FIG. 1E), and IgM antibody to native gliadin (FIG. 1F) in cohorts of healthy controls, celiac disease patients, and individuals identified as having NCWS. Horizontal red lines indicate the median for each cohort.

FIGS. 2A-F show markers of systemic immune response to microbial components. Serum levels of LBP (FIG. 2A), sCD14 (FIG. 2B), EndoCAb IgG (FIG. 2C), EndoCAb IgM (FIG. 2D), IgG antibody to flagellin (FIG. 2EA), and IgM antibody to flagellin (FIG. 2F) in cohorts of healthy controls, celiac disease patients, and individuals with NCWS. Horizontal red lines indicate the median for each cohort.

FIGS. 3A-C show intestinal epithelial cell damage and correlation with systemic immune activation. FIG. 3A shows serum levels of FABP2 in cohorts of healthy controls, celiac disease patients, and individuals identified as having NCWS. Correlation of serum levels of FABP2 with LBP (FIG. 3B) and sCD14 (FIG. 3C) in individuals with NCWS. Horizontal red lines indicate the median for each cohort.

FIGS. 5A-B show composite scores for intestinal symptoms (bloating, abdominal pain, diarrhea, epigastric pain, and nausea) and extra-intestinal symptoms (fatigue, headache, anxiety, memory and/or cognitive disturbances, and numbness in arms and/or legs) before and after 6 months of a diet free of wheat, rye, and barley in a cohort of 20 NCWS patients. FIGS. 5C-E show levels of IgG, IgA, and IgM antibody to gliadin proteins before and 6 months after starting the diet in the NCWS cohort. Each individual is represented by a dot and the two points corresponding to the same individual are connected by a line. Each box indicates the $25^{th}$-$75^{th}$ percentiles of distribution, with the horizontal line inside the box representing the median.

FIGS. 10A-B show correlation between serum levels of FABP2 and (FIG. 10A) EndoCAb IgM and (FIG. 10B) anti-flagellin IgM in individuals with NCWS.

DETAILED DESCRIPTION OF THE INVENTION

Figure 4:
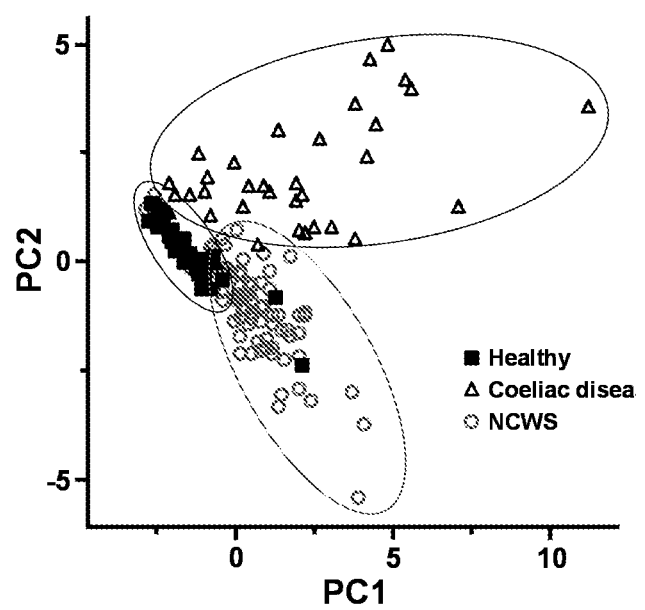
FIG. 4 shows PCA score plot for the complete dataset of serologic markers (anti-TG2 IgA; anti-deamidated gliadin IgG and IgA; anti-gliadin IgG, IgA, and IgM; LBP; sCD14; EndoCAb IgG, IgA, and IgM; anti-flagellin IgG, IgA, and IgM; and FABP2) measured in healthy controls, celiac disease patients, and individuals with NCWS. Subjects are plotted in two dimensions using the first and second principal components (PC1 and PC2).

In one embodiment, the present invention provides a method of identifying a subject having non-celiac wheat sensitivity, comprising the step of determining blood levels of one or more markers in said subject, said markers are soluble CD14 (sCD14), lipopolysaccharide-binding protein (LBP), anti-lipopolysaccharide antibodies, anti-flagellin antibodies, anti-gliadin antibodies, and/or intestinal fatty acid-binding protein (FABP2), wherein increased levels of a panel of said markers in the subject as compared to control levels indicate that said subject has non-celiac wheat sensitivity. In one embodiment, the levels of said markers are determined in serum or plasma. In one embodiment, the control levels are derived from healthy subjects or subjects having celiac disease. In one embodiment, the anti-lipopolysaccharide antibodies are IgM antibodies. In one embodiment, the anti-flagellin antibodies are IgM antibodies and/or IgG antibodies. In one embodiment, the anti-gliadin antibodies are IgG, IgA, and/or IgM antibodies.

In one embodiment, the above method would involve using a statistical algorithm (e.g. those based on a principal component discriminant statistical analysis or a similar method) of the above panel of biomarkers to predict whether said subject has non-celiac wheat sensitivity.

In one embodiment, the above method further comprises treating the identified subject with a gluten-free diet that eliminates wheat, rye, and/or barley, or any another treatment that is developed in the future. In one embodiment, the subject is treated with gluten-free diet for six months or more. In another embodiment, the subject is treated with gluten-free diet for less than six months.

Wheat is a complex substance, and one who has immune reactions or sensitivity to wheat may be reactive to one or more components of wheat. Currently, removal of the immunological trigger (wheat) is the basis of treatment once a NCWS patient is properly diagnosed. Alternative methods of treatment are being developed for wheat/gluten sensitivity. For example, approaches can be developed to target uptake of toxic wheat/gluten peptides by enhancing their enzymatic breakdown, by sequestering gluten proteins, or by restoring epithelial barrier function. One can also envision treating wheat/gluten sensitivity by hindering the activation of gluten-specific immune cells. Identification of gluten epitopes implicated in the immune response to gluten would open the possibility of devising methods for tolerizing some individuals with NCWS. Modulation of the immune system might also be possible in the future via, for example, anti-cytokine therapy.

In one embodiment, the present invention provides a method of providing a therapeutic intervention for a subject having NCWS, comprising first of identifying the subject with NCWS by determining blood levels of one or more markers in said subject, said markers are soluble CD14 (sCD14), lipopolysaccharide-binding protein (LBP), anti-lipopolysaccharide antibodies, anti-flagellin antibodies, anti-gliadin antibodies, and/or intestinal fatty acid-binding protein (FABP2), wherein increased levels of a panel of said markers in the subject as compared to control levels indicate that said subject has non-celiac wheat sensitivity. In one embodiment, the blood levels of said markers are determined in serum or plasma. In one embodiment, the control levels are derived from healthy subjects or subjects having celiac disease. In one embodiment, the anti-lipopolysaccharide antibodies are IgM antibodies. In one embodiment, the anti-flagellin antibodies are IgM antibodies and/or IgG antibodies. In one embodiment, the anti-gliadin antibodies are IgG, IgA, and/or IgM antibodies. The identified subject is then treated with a gluten-free diet, e.g. a diet that eliminates wheat, rye, and/or barley, or any another treatment that is devised in the future.

In another embodiment, the present invention provides a method of monitoring response to a treatment for non-celiac wheat sensitivity in a subject, comprising the step of determining blood levels of one or more markers in said subject before and after a treatment, said markers are anti-gliadin antibodies, soluble CD14 (sCD14), lipopolysaccharide-binding protein (LBP), anti-lipopolysaccharide antibodies, anti-flagellin antibodies, and/or intestinal fatty acid-binding protein (FABP2), wherein decreased levels of said markers in said subject after treatment indicate that the subject has responded to the treatment; otherwise the subject has not responded to the treatment. In one embodiment, the treatment comprises a diet free of one or more of wheat, rye and barley. In another embodiment, the treatment comprises any or all of currently available treatments or those developed in the future. In one embodiment, the anti-lipopolysaccharide antibodies are IgM antibodies. In one embodiment, the anti-flagellin antibodies are IgM antibodies and/or IgG antibodies. In one embodiment, the anti-gliadin antibodies are IgG, IgA, and/or IgM antibodies.

In another embodiment, the present invention provides a method of determining a treatment course for non-celiac wheat sensitivity in a subject, comprising the step of determining blood levels of one or more markers in said subject before and after a treatment, said markers are anti-gliadin antibodies (IgG, IgA, and/or IgM), soluble CD14 (sCD14), lipopolysaccharide-binding protein (LBP), anti-lipopolysaccharide IgM antibodies, anti-flagellin antibodies (IgG and/or IgM), and/or intestinal fatty acid-binding protein (FABP2), wherein decreased levels of said markers in said subject after treatment indicate that the subject has responded to the treatment and should continue to be treated with the treatment. Alternatively, if the levels of the markers do not decrease after treatment, it indicates that the subject has not responded to the treatment and should be treated with an alternative therapy. In one embodiment, the treatment comprises a diet free of one or more of wheat, rye and barley. In another embodiment, the treatment comprises any or all of currently available treatments or those developed in the future.

In another embodiment, the present invention provides a multi-analyte assay kit that aids in diagnosis of non-celiac wheat sensitivity in a subject. In one embodiment, the kit is an immunoassay kit comprising reagents that detect the presence of a panel of the markers disclosed herein. This assay can be in the form of ELISA, microarray, bead-based, or any other immunologic method that detects antibody-antigen interaction. In one embodiment, the kit includes isolated antibodies (e.g. monoclonal antibodies) specifically immunoreactive with a panel of the markers disclosed herein, and means for detecting the binding of the markers to the antibodies. In one embodiment, the antibodies are attached to a solid support, such as polymeric beads, dip sticks, 96-well plate or filter material. The detecting means of the kit may include labeled secondary antibodies. The solid surface reagent in the above kit can be prepared by any known techniques for attaching protein material to solid support material. For example, these attachment methods generally include non-specific adsorption of the protein to the support or covalent attachment of the protein, typically through a free amine group, to a chemically reactive group on the solid support, such as an activated carboxyl, hydroxyl, or aldehyde group. Optionally, the kit may further comprise a standard or control information so that the test sample can be compared with the control information standard to determine if the test amount of a marker detected in a sample is a diagnostic amount consistent with a diagnosis of non-celiac wheat sensitivity.

In one embodiment, the present invention provides a kit that aids in diagnosis of non-celiac wheat sensitivity in a subject, the kit comprises reagents that detect the presence of one or more markers in a sample from said subject, said markers are soluble CD14, lipopolysaccharide-binding protein (LBP), anti-lipopolysaccharide antibodies, anti-flagellin antibodies, anti-gliadin antibodies, and/or intestinal fatty acid-binding protein (FABP2). In one embodiment, the sample is a blood, serum or plasma sample. In one embodiment, the reagents are antibodies that specifically recognize one or more of the markers.

Example 1

Immune Activation in Non-Celiac Wheat Sensitivity

In the study described herein, we investigated 1) whether systemic immune activation in response to translocated microbial products may be a feature of NCWS, 2) whether such systemic immune activation is linked to a compromised intestinal epithelium, and 3) whether the systemic immune activation or damage to the epithelium is responsive to the elimination of wheat and related cereals from diet.

Methods

Patients and controls. The study included 80 individuals with NCWS who met the criteria recently proposed by an expert group[1] and who were identified using a previously described structured symptom questionnaire[2,3] (a modified version of the Gastrointestinal Symptom Rating Scale designed to rate symptoms commonly associated with NCWS). All NCWS subjects reported experiencing intestinal and/or extra-intestinal symptoms after ingestion of gluten-containing foods, including wheat, rye, or barley. The reported symptoms in all subjects improved or disappeared when those foods were withdrawn for a period of 6 months, and recurred when they were re-introduced for a period of up to 1 month. Individuals were excluded if they were already on a restrictive diet in the past 6 months, if they were positive for the celiac disease-specific IgA anti-endomysial and/or anti-TG2 autoantibody or for intestinal histologic findings characteristic of celiac disease, or if they were positive for wheat allergy-specific IgE serology or skin prick test. A total of 6 intestinal biopsies, including 2 from the duodenal bulb and 4 from the distal duodenum, were taken from each individual. Serum samples from all 80 NCWS subjects while on a diet that contained wheat, rye, and/or barley were available. In addition to the above specimens, serum samples were available from 20 of the above NCWS individuals both prior to and after 6 months of a self-monitored diet free of wheat, rye, and barley. These individuals were asked to complete the previously described questionnaire[3] prior to initiating the diet and immediately following its completion. For this study, specific intestinal symptoms (bloating, abdominal pain, diarrhea, epigastric pain, and nausea) and extra-intestinal symptoms (fatigue, headache, anxiety, memory and cognitive disturbances, and numbness in arms or legs), selected on the basis of being the most commonly reported symptoms by patients in this population as previously found[4], were considered for analysis. Symptoms were scored from 0 to 3 as follows: 0=absent; 1=occasionally present; 2=frequently present; and 3=always present. A total score, based on the sum of individual symptom scores, was calculated for each individual at the two time points (before and after the diet). The study also included 40 serum samples from patients with biopsy-proven active celiac disease and 40 serum samples from healthy subjects (both groups on normal non-restrictive diet), recruited as part of the same protocol that included the NCWS individuals. All cases of celiac disease were biopsy-proven and diagnosed according to established criteria.[5] Screening questionnaires were used to evaluate the general health of unaffected controls. Individuals who had a history of liver disease, liver function blood test results (AST (aspartate transaminase), ALT (alanine transaminase), ALP (alkaline phosphatase), total protein, albumin, globulin, and bilirubin) outside the normal range, or a recent infection were excluded from all cohorts in the study.

All samples were collected with written informed consent under institutional review board-approved protocols at St. Orsola-Malpighi Hospital, Bologna, Italy. Serum specimens were kept at −80° C. to maintain stability. This study was approved by the Institutional Review Board of Columbia University Medical Center.

Assays.

Established serologic markers of celiac disease, including IgA antibody to TG2 and IgG and IgA antibodies to deamidated gliadin, were measured as previously described.[6,7]

Serum IgG, IgA, and IgM antibodies to native gliadin were measured separately by the enzyme-linked immunosorbent assay (ELISA) as previously described,[6,8] with the following modification: the secondary antibodies were HRP-conjugated anti-human IgG (GE Healthcare), IgA (MP Biomedicals), or IgM (MP Biomedicals). Serum IgG, IgA, and IgM antibodies to bacterial flagellin were measured separately using a similar protocol for detecting antibodies to gliadin, with the following modification: plates were coated with a 2 µg/mL solution of highly purified flagellin from *Salmonella typhimurium* (InvivoGen).

Levels of serum IgG, IgA, and IgM endotoxin-core antibodies (EndoCAb) (Hycult Biotech), lipopolysaccharide (LPS)-binding protein (LBP) (Hycult Biotech), soluble CD14 (sCD14) (R&D Systems), and intestinal fatty acid-binding protein (FABP2) (R&D Systems) were determined by ELISA, according to the manufacturers' protocols.

Data Analysis.

Group differences were analyzed by the Kruskal-Wallis one-way analysis of variance, with post-hoc testing and correction for multiple comparisons. Correlation analysis was performed using Spearman's r. A multivariate principal component analysis (PCA) was carried out on the entire dataset to reduce data dimensionality and to assess clustering. The effect of the restrictive diet was assessed by the Wilcoxon matched-pairs test. All P values were 2-sided, and differences were considered statistically significant at $P<0.05$. Statistical analyses were performed with Prism 6 (GraphPad) and Minitab 17 (Minitab) software.

Results

Patients and Controls.

The demographic and clinical characteristics of the study cohorts are included in Table 1. Twenty-one (26%) NCWS individuals carried the HLA DQ2 and/or DQ8 genes, a rate not substantially different than in the general population. Small intestine duodenal biopsy showed a normal mucosa (Marsh 0) in 48 (60%) and mild abnormalities, represented by an increased intraepithelial lymphocyte number (Marsh 1), in 32 (40%). In contrast, all celiac disease patients in this study carried the HLA DQ2 and/or DQ8 markers and presented with Marsh 3 grade intestinal histologic findings.

TABLE 1

Demographic and clinical characteristics of study cohorts.

| Subject group | Number of subjects | Mean age, years [SD] | Females no. (%) | Celiac disease-associated HLA DQ2 and/or DQ8-no. (%) | Intestinal biopsy histologic grade: Marsh 0; Marsh 1; Marsh 3-no. (%) |
|---|---|---|---|---|---|
| NCWS | | | | | |
| Non-restrictive diet | 80 | 34.6 [10.3] | 62 (78) | 21 (26) | 48 (60); 32 (40); 0 |
| Before and after restrictive diet* | 20 | 34.0 [10.7] | 19 (95) | 7 (35) | 9 (45); 11 (55); 0 |
| Active celiac disease | 40 | 34.5 [13.7] | 30 (75) | 40 (100) | 0, 0, 40 (100) |
| Healthy | 40 | 35.0 [12.8] | 30 (75) | — | — |

*Intestinal biopsy taken prior to dietary restriction.

Markers of Celiac Disease and Immune Reactivity to Gluten.

As expected, only the active celiac disease patients exhibited significantly elevated IgA antibody reactivity to TG2, as well as IgG and IgA antibody reactivity to deamidated gliadin, when compared with healthy controls (P<0.0001 for each comparison) (FIG. 1A-C). Celiac disease patients also displayed increased IgG and IgA (P<0.0001 for each), but not IgM, antibody reactivity to native gliadin when compared to healthy controls (FIG. 1D-F). In the NCWS cohort (while being on a diet that did not restrict the intake of wheat and related cereals), IgG, IgA, and IgM antibodies to native gliadin were all significantly higher than in the healthy control group (P<0.0001, P<0.0001, and P=0.018 respectively) (FIG. 1D-F). However, IgA reactivity to native gliadin in this NCWS cohort was lower than in the celiac disease group (P=0.015). There was no association between antibody reactivity to native gliadin and the presence of HLA-DQ2 and/or DQ8 genes in the NCWS group.

Systemic Innate Immune Activation.

Figure 7:
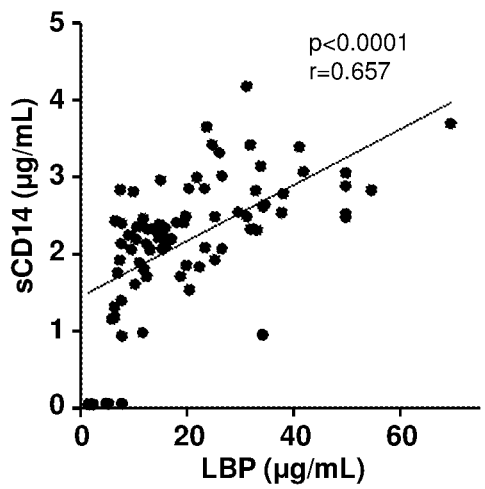
FIG. 7 shows correlation between serum levels of LBP and sCD14 in individuals with NCWS.

Serum levels of both LBP and sCD14 were significantly elevated in individuals with NCWS in comparison to celiac disease patients and healthy individuals (P<0.0001 for each comparison) (FIG. 2A-B). There was a highly significant correlation between serum LBP and sCD14 (r=0.657, P<0.0001) (FIG. 7). Neither LBP nor sCD14 was found to be significantly elevated in celiac disease patients when compared to healthy controls.

B Cell Response to Microbial Antigens.

Figure 8:
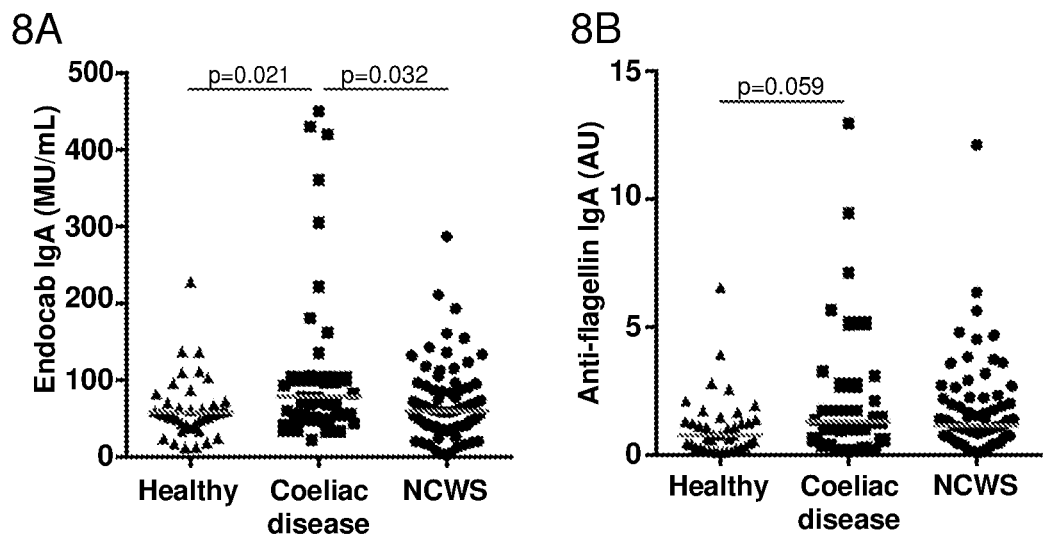
FIGS. 8A-B show IgA responses to LPS and flagellin. Serum levels of EndoCAb IgA (FIG. 8A) and IgA antibody to flagellin (FIG. 8B) in cohorts of healthy controls, celiac disease patients, and individuals identified as having NCWS. Horizontal red lines indicate the median for each cohort.

When compared with the healthy control and celiac disease cohorts, the NCWS group had significantly higher levels of EndoCAb IgM (P<0.0001 and P=0.028, respectively) (FIG. 2D), but not IgG or IgA (FIG. 2C; FIG. 8A). In contrast to the NCWS cohort, the celiac disease group had higher levels of EndoCAb IgA when compared with the NCWS and healthy control groups (P=0.021 and P=0.032, respectively) (FIG. 8A), but not IgG or IgM (FIG. 2C-D).

Figure 9:
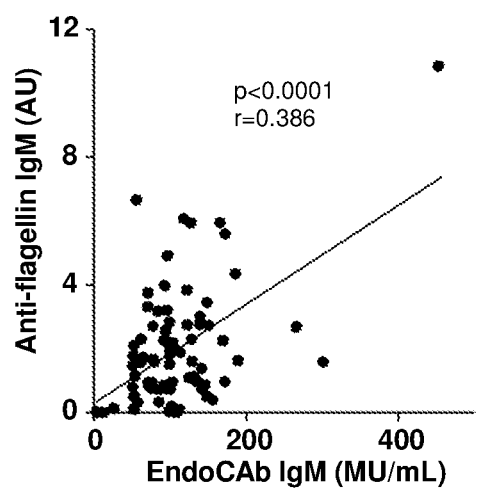
FIG. 9 shows correlation between serum levels of EndoCAb IgM and anti-flagellin IgM in NCWS individuals.

Furthermore, the levels of IgG and IgM antibodies to flagellin were significantly elevated in the NCWS cohort when compared with the healthy control group (P=0.001 and P=0.009, respectively) (FIG. 2E-F). These antibodies were not significantly elevated in the celiac disease cohort, although there was a trend towards higher IgA reactivity to flagellin when compared with healthy controls (P=0.059) (FIG. 8B). The increased IgM antibody response to flagellin correlated with the elevated EndoCAb IgM in the NCWS cohort (r=0.386, P<0.0001) (FIG. 9).

Systemic Immune Activation is Associated with Increased Intestinal Epithelial Cell Damage.

Figure 11:
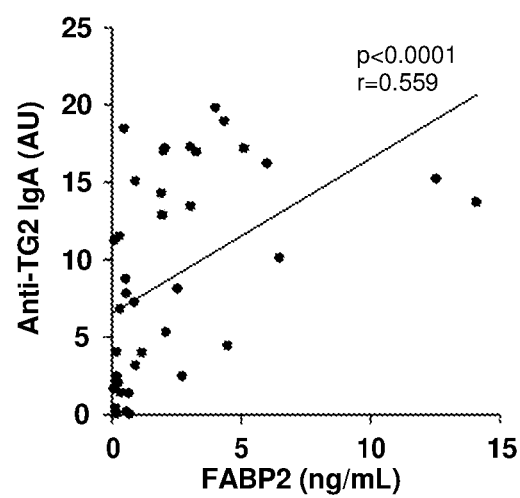
FIG. 11 shows correlation between serum levels of FABP2 and IgA antibody to TG2 in patients with celiac disease.

In comparison with the healthy control group, serum concentrations of FABP2, a marker of intestinal epithelial cell damage, were significantly elevated in the NCWS cohort, as well as in the celiac disease group (P<0.0001 for each) (FIG. 3A). In addition, the FABP2 concentrations in the NCWS cohort correlated with levels of LBP (r=0.360, P=0.001) and sCD14 (r=0.461, P<0.0001) (FIG. 3B-C). The FABP2 concentrations in the NCWS group also correlated with EndoCAb IgM (r=0.326, P=0.003) and anti-flagellin IgM antibody reactivity (r=−0.239, P=0.03) in the NCWS cohort (FIG. 10A-B). In the celiac disease cohort, FABP2 concentrations correlated with the levels of IgA antibody to TG2 (r=0.559, P<0.0001) (FIG. 11).

Multivariate Analysis of Dataset.

PCA was used to assess similarities and differences between the subjects in the three cohorts based on the generated data and to determine whether they can be grouped. Most of the variability in the data could be explained by the first two components (54%). The score plot of the first and second components for the entire dataset demonstrated the clustering of the healthy control, celiac disease, and NCWS subjects into three discernible groups, with some outliers (FIG. 4).

Systemic Immune Activation and Intestinal Epithelial Cell Damage Respond to Dietary Restriction.

Figure 5:
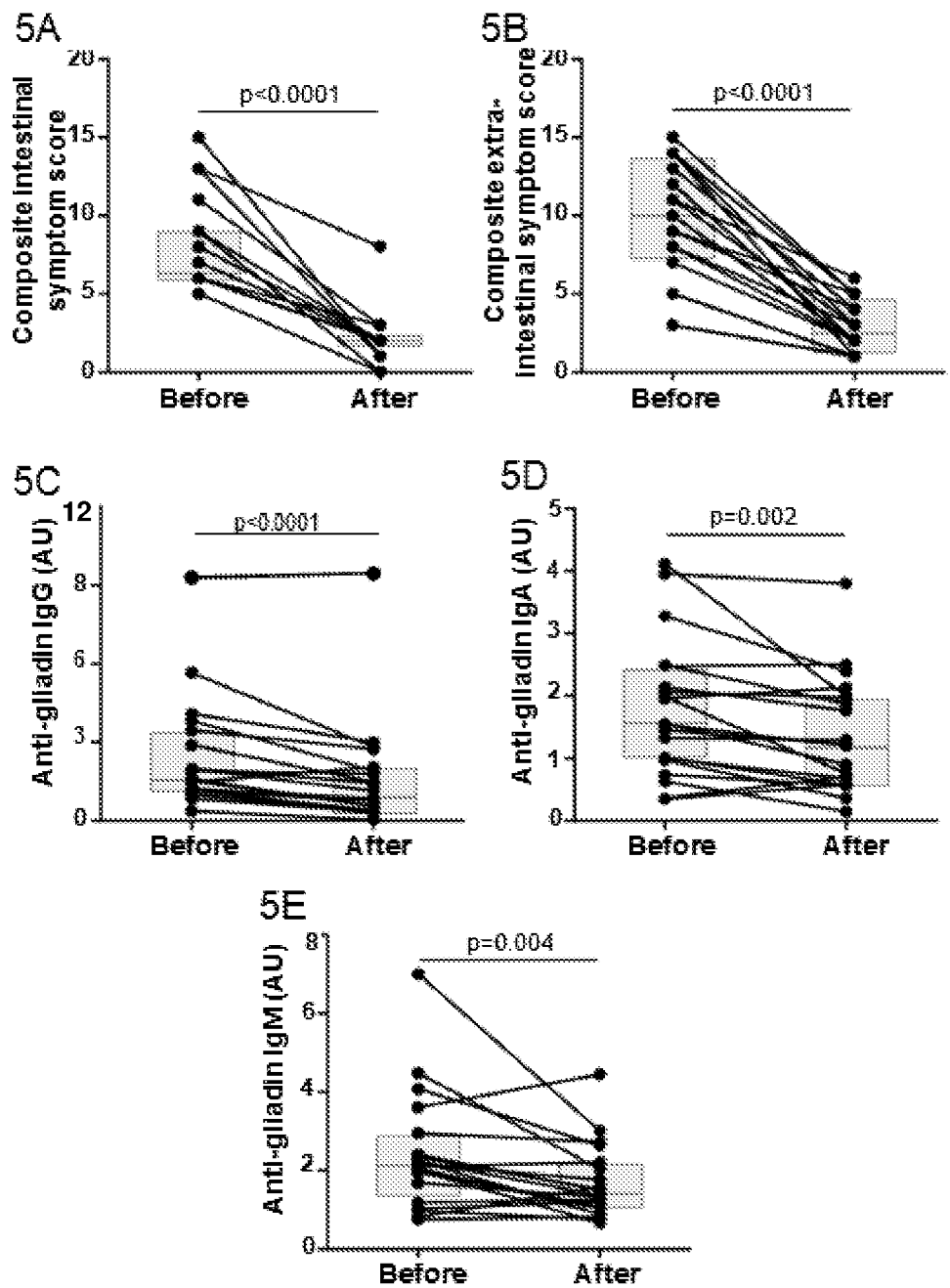
FIGS. 5A-E show symptoms and anti-gliadin antibody reactivity in response to restrictive diet.
Figure 6:
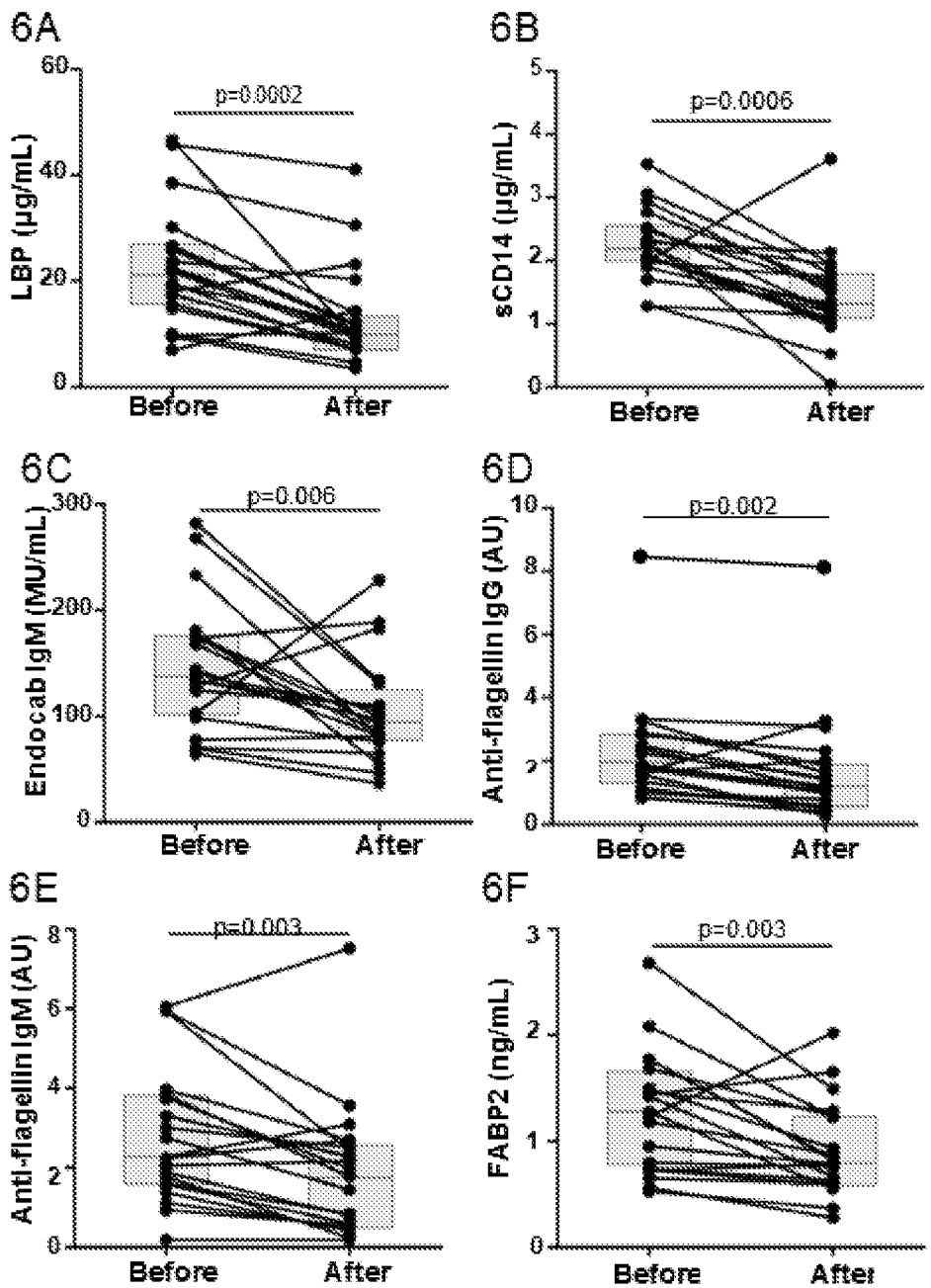
FIGS. 6A-F show markers of intestinal epithelial cell damage and systemic immune activation in response to the restrictive diet. Levels of LBP, sCD14, EndoCAb IgM, anti-flagellin IgG, anti-flagellin IgM, and FABP2 before and 6 months of a diet free of wheat, rye, and barley in the cohort of 20 NCWS patients are shown. Each individual is represented by a dot and the two points corresponding to the same individual are connected by a line. Each box indicates the $25^{th}$-$75^{th}$ percentiles of distribution, with the horizontal line inside the box representing the median.

Levels of the above markers of immune activation and gut epithelial cell damage were also measured in 20 of the above NCWS subjects before and 6 months after initiation of a diet free of wheat, rye, and barley. All individuals reported symptom improvement at the end of 6 months, which was reflected in a significant reduction in both the intestinal and extra-intestinal composite symptom scores (P<0.0001 for each) (FIG. 5A-B), accompanied by a decline in IgG, IgA, and IgM anti-gliadin antibodies (P<0.0001, P=0.002, and P=0.004, respectively) (FIG. 5C-E). In conjunction with this, we found a statistically significant reduction in the serum levels of LBP (P=0.0002), sCD14 (P=0.0006), EndoCAb IgM (P=0.006), anti-flagellin IgG and IgM antibodies (P=0.002 and P=0.003, respectively), and FABP2 (P=0.003) after the completion of the diet (FIG. 6A-F). The magnitude of change in the measured biological markers did not correlate significantly with that for the symptom scores.

DISCUSSION

As expected, individuals with sensitivity to wheat in the absence of celiac disease did not exhibit significantly elevated antibody responses to TG2 or deamidated gliadin sequences. This indicates that in contrast to celiac disease, the observed humoral immune response to gluten in NCWS is independent of TG2 enzymatic activity and HLA-DQ2/DQ8, and is likely to target certain epitopes that are distinct from those in celiac disease. We hypothesized that the enhanced antibody response to native gliadin in NCWS individuals, particularly IgG and IgM isotypes, may be a consequence of ongoing intestinal epithelial barrier defects. If so, such defects might also give rise to an inadequate regulation of the interaction between the gut microbiota and systemic circulation, resulting in peripheral immune activation. To examine this, we measured the levels of LBP and sCD14 as indicators of the translocation of microbial products, particularly LPS, across the epithelial barrier. Translocated circulating LPS can result in the rapid secretion of LBP by gastrointestinal and hepatic epithelial cells, as well as sCD14 by CD14+ monocytes/macrophages.[9] sCD14 binds LPS in the presence of LBP to activate TLR4.[10] We found significantly elevated serum levels of both LBP and sCD14 in individuals with NCWS in comparison to celiac disease patients and healthy controls. The high degree of correlation between serum LBP and sCD14 suggested that these molecules are concurrently expressed in response to the stimulus in NCWS individuals.

We also quantified serum levels of antibody to LPS core oligosaccharide, or EndoCAb, which is known to modulate in response to bacterial endotoxin in circulation.[11] As they are involved in the neutralization of circulating endotoxin, EndoCAb immunoglobulins are typically depleted in response to an acute LPS exposure, but eventually rise due to the B cell anamnestic response.[19] Individuals in the NCWS cohort exhibited increased levels of EndoCAb IgM. To demonstrate that the systemic immune response in individuals identified as having NCWS would not be limited to only LPS if driven by translocated microbial products, we also measured serum levels of antibody to flagellin, the principal substituent protein of the flagellum in Grampositive and-negative bacteria. We found that levels of IgG and IgM antibodies to flagellin were significantly elevated in the NCWS cohort. Considering that no individuals in this study had evidence of infection, these observations are suggestive of a translocation of microbial products from the gastrointestinal tract that contributes to the observed innate and adaptive immune activation in the NCWS cohort.

Circulating bacterial components, such as LPS and flagellin, bind to their respective TLRs on various cells, including macrophages and dendritic cells, which results in signaling through the myeloid differentiation factor 88 (MyD88) adaptor protein.[10] Ultimately, MyD88 signaling leads to the activation of transcription factor nuclear factor-κB (NF-κB) and increased expression of various pro-inflammatory cytokines that can exert deleterious systemic effects.[9, 12] A systemic innate immune activation model would be consistent with the generally rapid onset of reported symptoms in NCWS.[4] In addition, circulating microbial products can bind to TLRs on other cells to trigger a more localized inflammatory response. For example, LPS binds directly to TLR4 on the luminal surface of brain blood vessels, resulting in local cytokine secretion in the brain that has been shown to activate the microglia to displace inhibitory synapses.[13] In HIV infection, where the presence of microbial translocation is linked to intestinal epithelial damage, increased systemic immune activation in response to bacterial antigens is associated with cognitive deficits.[14] Such a pathway might contribute to some of the neurocognitive symptoms experienced by NCWS individuals.

Subsequently, we hypothesized that the observed systemic immune activation in response to microbial products in individuals with NCWS may be linked to increased intestinal enterocyte damage and turnover rate. FABP2 is a cytosolic protein specific to intestinal epithelial cells that is rapidly released into systemic circulation upon cellular damage.[15] Alterations in circulating FABP2 concentration, reflecting epithelial cell loss and changes in enterocyte turnover rate, are useful for identifying acute intestinal injury.[15-18] Elevated circulating FABP2 has been shown to be associated with increasing degrees of villous atrophy in celiac disease,[19] and with microbial translocation in HIV[20] that is in turn linked to damaged intestinal epithelial barrier integrity.[21] Similar to the celiac disease patients, the NCWS individuals in this study were found to have raised circulating FABP2 levels, indicating increased intestinal epithelial cell damage. FABP2 concentrations in the NCWS cohort correlated strongly with levels of LBP and sCD14, suggesting a link between the intestinal epithelial cell damage and the acute systemic immune activation in response to translocated microbial products. The FABP2 concentrations in the NCWS group also correlated with IgM antibody reactivity towards microbial antigens, though less strongly in comparison to LBP and sCD14 responses, as might be expected for a systemic antibody response. In the celiac disease cohort, FABP2 concentrations correlated with the increased IgA antibody to TG2, confirming the existence of a close relationship between the mucosal autoimmune response and the intestinal damage in this disease.

In contrast to celiac disease, however, investigations of small intestine biopsies in NCWS subjects in this and other studies have not found villous atrophy or mucosal architectural abnormalities,[2, 4, 22, 23] even if significant inflammatory changes are seen.[23] One possible explanation for this could be that the epithelial damage associated with NCWS is in regions other than the duodenum from where biopsies are generally taken in such individuals. This would be plausible because FABP2 is expressed primarily by the epithelial cells of the jejunum,[16, 24] which may point to this region of the small intestine as a potential primary site of mucosal damage in NCWS. Different sections of the gastrointestinal tract have unique cellular, structural, and immunologic features that make them vulnerable to specific insults.[25] Another possibility is that the epithelial changes associated with NCWS might be more subtle in comparison to celiac disease, without overt remodeling of the mucosa. For example, TNF-α-mediated enhancement of enterocyte loss has been shown to cause mucosal barrier dysfunction and physical gaps in the epithelium that require confocal and scanning electron microscopy for visualization.[26]

On the other hand, despite the established extensive villus damage associated with celiac disease, neither LBP nor sCD14 levels were found to be significantly elevated in the celiac disease group, thus standing in stark contrast to the NCWS cohort. In addition, among the immunoglobulin responses to microbial antigens, only IgA antibodies appeared to be increased in celiac disease. These data suggest that there is an effective mechanism for the neutralization of microbial products that may cross into the lamina propria in most cases of celiac disease, possibly in part via the localized IgA response and mucosal phagocytic cells. These mechanisms are known to be essential for the immune surveillance of luminal antigens and the elimination of microbial products that cross the epithelial barrier, thereby reducing the likelihood of their translocation into the submucosa and access to blood vessels.[9] Such mucosal immune responses may be lacking or inadequate in individuals with NCWS. Instead, what we observed were enhanced IgM responses to gliadin, LPS, and flagellin in the NCWS cohort, which clearly contrasted with the celiac disease group. In humans, IgM memory B cells are present in the peripheral blood and contribute to the expression of IgM antibodies to a diverse variety of antigens, offering a first line of defense against potential pathogens.[27] Exposure to unmethylated CpG sequences, which are abundant in the bacterial and viral genomes, can result in TLR9-dependent proliferation and differentiation of these B cells, independent of direct interaction with their respective antigens or T cell involvement.[28] Acute microbial translocation from the gut, as the data from our study suggest, would be expected to enhance the secretion of IgM antibodies in the periphery via this pathway. These IgM B cells would be additionally stimulated upon encounter with specific antigens, such as the translocated microbial components or gliadin sequences, and may contribute to the observed IgM antibody responses.[28, 29] Recognition and agglutination of antigens by IgM and IgG antibodies can result in the activation of the classical complement pathway and Fc receptor-mediated endocytosis by macrophages,[30] further contributing to the ongoing systemic immune response.

The hallmark of NCWS is the onset of intestinal and/or extra-intestinal symptoms upon ingestion of gluten-containing foods, i.e., wheat, rye, and barley, and the alleviation of symptoms upon their withdrawal from diet. To determine whether the patient-reported symptom resolution upon the elimination of these foods would be associated with the amelioration of intestinal epithelial cell damage and a reduction in microbial translocation and systemic immune activation, we examined the above markers in a subset of NCWS subjects prior to and after a diet that excluded wheat and related cereals. The results indicated a significant decline in the markers of immune activation and gut epithelial cell damage, in conjunction with the improvement of symptoms. However, the magnitude of change in the measured biological markers did not correlate significantly with that for the symptom scores. This appears to be similar to observations in celiac disease patients, where symptoms are known to be a poor predictor of disease activity and associated biomarkers.[31, 32] A limitation of this portion of the study was the absence of a healthy control group to assess the potential impact of the dietary restriction in unaffected individuals.

In summary, the results of this study on individuals with sensitivity to wheat in the absence of celiac disease demonstrate 1) significantly increased serum levels of sCD14 and LBP, as well as antibody reactivity to microbial antigens, indicating systemic immune activation, 2) an elevated expression of FABP2 that correlates with the systemic immune responses to bacterial products, suggesting compromised intestinal epithelial barrier integrity and increased microbial translocation, and 3) a significant change towards normalization in the levels of the immune activation markers, as well as FABP2 expression, in response to the restrictive diet, which is associated with improvement in symptoms. Our data establish the presence of objective markers of systemic immune activation and epithelial cell damage in the affected individuals. The results of the multivariate data analysis suggest that a selected panel of these may have utility for identifying NCWS patients or patient subsets in the future.

REFERENCES

1. Catassi C, Elli L, Bonaz B, et al. Diagnosis of non-celiac gluten sensitivity (NCGS): the Salerno experts' criteria. Nutrients 2015; 7:4966-77.
2. Caio G, Volta U, Tovoli F, et al. Effect of gluten free diet on immune response to gliadin in patients with non-celiac gluten sensitivity. BMC Gastroenterol 2014; 14:26.
3. Volta U, Caio G, De Giorgio R, et al. Non-celiac gluten sensitivity: a work-in-progress entity in the spectrum of wheat-related disorders. Best Pract Res Clin Gastroenterol 2015; 29:477-91.
4. Volta U, Bardella M T, Calabro A, et al. An Italian prospective multicenter survey on patients suspected of having non-celiac gluten sensitivity. BMC Med 2014; 12:85.
5. Rubio-Tapia A, Hill I D, Kelly C P, et al. ACG clinical guidelines: diagnosis and management of celiac disease. Am J Gastroenterol 2013; 108:656-76.
6. Moeller S, Canetta P A, Taylor A K, et al. Lack of serologic evidence to link IgA nephropathy with celiac disease or immune reactivity to gluten. PLoS One 2014; 9:e94677.
7. Lau N, Green P H, Taylor A K, et al. Markers of celiac disease and gluten sensitivity in children with autism. PLoS One 2013; 8:e66155.
8. Huebener S, Tanaka C K, Uhde M, et al. Specific nongluten proteins of wheat are novel target antigens in celiac disease humoral response. J Proteome Res 2015; 14:503-11.
9. Brenchley J M, Douek D C. Microbial translocation across the GI tract. Annu Rev Immunol 2012; 30:149-73.
10. Miller S I, Ernst R K, Bader M W. LPS, TLR4 and infectious disease diversity. Nat Rev Microbiol 2005; 3:36-46.
11. Barclay G R. Endogenous endotoxin-core antibody (EndoCAb) as a marker of endotoxin exposure and a prognostic indicator: a review. Prog Clin Biol Res 1995; 392:263-72.
12. Akira S, Takeda K. Toll-like receptor signalling. Nat Rev Immunol 2004; 4:499-511.
13. Chen Z, Jalabi W, Shpargel K B, et al. Lipopolysaccharide-induced microglial activation and neuroprotection against experimental brain injury is independent of hematogenous TLR4. J Neurosci 2012; 32:11706-15.
14. Sandler N G, Douek D C. Microbial translocation in HIV infection: causes, consequences and treatment opportunities. Nat Rev Microbiol 2012; 10:655-66.
15. Pelsers M M, Hermens W T, Glatz J F. Fatty acid-binding proteins as plasma markers of tissue injury. Clin Chim Acta 2005; 352:15-35.
16. Pelsers M M, Namiot Z, Kisielewski W, et al. Intestinal-type and liver-type fatty acid-binding protein in the intestine. Tissue distribution and clinical utility. Clin Biochem 2003; 36:529-35.
17. Sandler N G, Koh C, Roque A, et al. Host response to translocated microbial products predicts outcomes of patients with HBV or HCV infection. Gastroenterology 2011; 141:1220-30.
18. Sacchettini J C, Hauft S M, Van Camp S L, et al. Developmental and structural studies of an intracellular lipid binding protein expressed in the ileal epithelium. J Biol Chem 1990; 265:19199-207.
19. Adriaanse M P, Tack G J, Passos V L, et al. Serum I-FABP as marker for enterocyte damage in coeliac disease and its relation to villous atrophy and circulating autoantibodies. Aliment Pharmacol Ther 2013; 37:482-90.
20. Hunt P W, Sinclair E, Rodriguez B, et al. Gut epithelial barrier dysfunction and innate immune activation predict mortality in treated HIV infection. J Infect Dis 2014; 210:1228-38.
21. Estes J D, Harris L D, Klatt N R, et al. Damaged intestinal epithelial integrity linked to microbial translocation in pathogenic simian immunodeficiency virus infections. PLoS Pathog 2010; 6:e1001052.
22. Shahbazkhani B, Sadeghi A, Malekzadeh R, et al. Non-Celiac Gluten Sensitivity Has Narrowed the Spectrum of Irritable Bowel Syndrome: A Double-Blind Randomized Placebo-Controlled Trial. Nutrients 2015; 7:4542-54.
23. Carroccio A, Mansueto P, Iacono G, et al. Non-celiac wheat sensitivity diagnosed by double-blind placebo-controlled challenge: exploring a new clinical entity. Am J Gastroenterol 2012; 107:1898-906.
24. Derikx J P, Vreugdenhil A C, Van den Neucker A M, et al. A pilot study on the noninvasive evaluation of intestinal damage in celiac disease using I-FABP and L-FABP. J Clin Gastroenterol 2009; 43:727-33.
25. Cossart P, Sansonetti P J. Bacterial invasion: the paradigms of enteroinvasive pathogens. Science 2004; 304: 242-8.
26. Kiesslich R, Goetz M, Angus E M, et al. Identification of epithelial gaps in human small and large intestine by confocal endomicroscopy. Gastroenterology 2007; 133: 1769-78.
27. Lanzavecchia A, Bernasconi N, Traggiai E, et al. Understanding and making use of human memory B cells. Immunol Rev 2006; 211:303-9.
28. Capolunghi F, Rosado M M, Sinibaldi M, et al. Why do we need IgM memory B cells? Immunol Lett 2013; 152: 114-20.
29. Bailey M, Haverson K, Miller B, et al. Effects of infection with transmissible gastroenteritis virus on concomitant immune responses to dietary and injected antigens. Clin Diagn Lab Immunol 2004; 11:337-43.

30. Ehrenstein M R, Notley C A. The importance of natural IgM: scavenger, protector and regulator. Nat Rev Immunol 2010; 10:778-86.
31. Katz K D, Rashtak S, Lahr B D, et al. Screening for celiac disease in a North American population: sequential serology and gastrointestinal symptoms. Am J Gastroenterol 2011; 106:1333-9.
32. Leffler D A, Dennis M, Hyett B, et al. Etiologies and predictors of diagnosis in nonresponsive celiac disease. Clin Gastroenterol Hepatol 2007; 5:445-50.

What is claimed is:

1. A method of treating a human subject having non-celiac wheat sensitivity in the absence of celiac disease, comprising:
   i. detecting blood levels of one or more markers in said human subject, said markers are selected from the group consisting of soluble CD 14, lipopolysaccharide-binding protein (LBP), anti-lipopolysaccharide antibodies, anti-flagellin antibodies, and intestinal fatty acid-binding protein (FABP2), wherein increased levels of said markers in said human subject as compared to levels of said markers in human subjects having celiac disease indicate said human subject has non-celiac wheat sensitivity in the absence of celiac disease; and
   ii. treating the human subject identified in (i) with a diet free of one or more of wheat, rye and barley.

2. The method of claim 1, wherein levels of said markers are determined in serum or plasma.

3. The method of claim 1, wherein said anti-lipopolysaccharide antibodies are IgM antibodies.

4. The method of claim 1, wherein said anti-flagellin antibodies are one or both of IgM antibodies and IgG antibodies.

* * * * *